(12) United States Patent
Dittman (10) Patent No.: US 7,651,519 B2
(45) Date of Patent: Jan. 26, 2010

(54) PROSTHESIS DEPLOYMENT SYSTEM

(75) Inventor: Jay A. Dittman, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 297 days.

(21) Appl. No.: 10/930,523

(22) Filed: Aug. 31, 2004

(65) Prior Publication Data

US 2005/0060018 A1    Mar. 17, 2005

Related U.S. Application Data

(60) Provisional application No. 60/503,375, filed on Sep. 16, 2003.

(51) Int. Cl.
*A61F 2/84* (2006.01)
(52) U.S. Cl. ..................... 623/1.11; 623/1.23
(58) Field of Classification Search ....... 623/1.11–1.13, 623/1.23; 606/108
See application file for complete search history.

(56) References Cited

U.S. PATENT DOCUMENTS

| 4,562,596 | A | | 1/1986 | Kornberg | |
|---|---|---|---|---|---|
| 4,665,918 | A | | 5/1987 | Garza et al. | |
| 4,787,899 | A | * | 11/1988 | Lazarus | 623/1.11 |
| 4,950,227 | A | | 8/1990 | Savin et al. | |
| 5,201,757 | A | * | 4/1993 | Heyn et al. | 606/198 |
| 5,387,235 | A | | 2/1995 | Chuter | |
| 5,480,423 | A | * | 1/1996 | Ravenscroft et al. | 623/1.11 |
| 5,484,444 | A | * | 1/1996 | Braunschweiler et al. | 623/1.11 |
| 5,628,783 | A | | 5/1997 | Quiachon et al. | |
| 5,693,083 | A | * | 12/1997 | Baker et al. | 623/1.11 |
| 5,702,418 | A | * | 12/1997 | Ravenscroft | 623/1.11 |
| 5,709,703 | A | * | 1/1998 | Lukic et al. | 623/1.12 |
| 5,720,776 | A | | 2/1998 | Chuter et al. | |
| 5,824,058 | A | * | 10/1998 | Ravenscroft et al. | 623/1.11 |
| 6,190,393 | B1 | * | 2/2001 | Bevier et al. | 606/108 |
| 6,206,931 | B1 | | 3/2001 | Cook et al. | |
| 6,346,118 | B1 | * | 2/2002 | Baker et al. | 623/1.12 |
| 6,425,898 | B1 | * | 7/2002 | Wilson et al. | 606/108 |
| 7,056,337 | B2 | | 6/2006 | Boatman | 623/1.15 |
| 7,081,132 | B2 | | 7/2006 | Cook et al. | 623/1.36 |
| 7,118,600 | B2 | | 10/2006 | Dua et al. | 623/23.68 |
| 7,153,324 | B2 | | 12/2006 | Case et al. | 623/1.24 |
| 7,160,318 | B2 | | 1/2007 | Greenberg et al. | 623/1.16 |
| 2002/0099432 | A1 | | 7/2002 | Yee | |
| 2003/0233140 | A1 | | 12/2003 | Hartley et al. | |
| 2004/0054396 | A1 | | 3/2004 | Hartley et al. | |
| 2004/0098079 | A1 | | 5/2004 | Hartley et al. | |

FOREIGN PATENT DOCUMENTS

| EP | 0 684 022 A2 | 11/1995 |
|---|---|---|
| WO | WO 98/53761 | 12/1998 |
| WO | WO 99/29262 | 6/1999 |
| WO | WO 03/034948 A1 | 5/2003 |
| WO | WO 03/053287 A1 | 7/2003 |

* cited by examiner

*Primary Examiner*—Anhtuan T Nguyen
*Assistant Examiner*—Ryan J Severson
(74) *Attorney, Agent, or Firm*—Brinks Hofer Gilson & Lione (57) ABSTRACT

An introducer for an expandable endovascular prosthesis having a self expanding stent has a distal prosthesis positioning mechanism and a proximal prosthesis retention mechanism. The proximal prosthesis retention mechanism includes a cylindrical sleeve adapted to retain the self expanding stent. A release mechanism extends proximally from the distal prosthesis positioning mechanism and exerts a force in the proximal direction on an interior surface of the self expanding stent to retain the self expanding stent in the cylindrical sleeve.

28 Claims, 11 Drawing Sheets

PROSTHESIS DEPLOYMENT SYSTEM

CROSS-REFERENCE TO RELATED APPLICATIONS

This application is based on and claims all benefits of Provisional Application Ser. No. 60/503,375 filed Sep. 16, 2003.

BACKGROUND OF THE INVENTION

1. Technical Field

This invention relates to a medical device and, in particular, a method and means for retaining and releasing an expandable, intraluminal prosthesis for the endovascular repair of diseased or damaged vessels.

Throughout this specification the terms proximal and proximally are used for a position or direction towards the patient's heart and the terms distal and distally are used for a position or direction away the patient's heart.

2. Related Art

The deployment of intraluminal prostheses into the lumen of a patient from a remote location by the use of a deployment device or introducer has been disclosed in a number of earlier patents and patent applications. U.S. Pat. No. 4,562,596 entitled "Aortic Graft, Device and Method for Performing an Intraluminal Abdominal Aortic Aneurysm Repair", which is herein incorporated by reference, proposes the retention of a self expanding graft within a sleeve until it is to be deployed, at which time the sleeve is withdrawn and the graft is allowed to expand. U.S. Pat. No. 4,665,918 entitled "Prosthesis System and Method", which is herein incorporated by reference, proposes a system and method for the deployment of a prosthesis in a blood vessel. The prosthesis is positioned between a delivery catheter and an outer sheath and expands outwardly upon removal of the sheath.

U.S. Pat. No. 4,950,227 entitled "Stent Delivery System", which is herein incorporated by reference, proposes the delivery of a stent by mounting the stent to the outside of an inflatable catheter and retaining the ends of an unexpanded stent by fitting a sleeve over either end of the stent. Expansion of the stent is caused by inflation of the catheter between the sleeves so that the ends of the stent are withdrawn from the respective sleeves and the stent released and expanded into position.

U.S. Pat. No. 5,387,235 entitled "Expandable Transluminal Graft Prosthesis for Repair of Aneurysm", discloses apparatus and methods of retaining grafts onto deployment devices. These features and other features disclosed in U.S. Pat. No. 5,387,235 could be used with the present invention, and the disclosure of U.S. Pat. No. 5,387,235 is herein incorporated by reference.

U.S. Pat. No. 5,720,776 entitled "Barb and Expandable Transluminal Graft Prosthesis for Repair of Aneurysm" discloses improved barbs with various forms of mechanical attachment to a stent. These features and other features disclosed in U.S. Pat. No. 5,720,776 could be used with the present invention, and the disclosure of U.S. Pat. No. 5,720,776 is herein incorporated by reference.

U.S. Pat. No. 6,206,931 entitled "Graft Prosthesis Materials" discloses graft prosthesis materials and a method for implanting, transplanting replacing and repairing a part of a patient and particularly the manufacture and use of a purified, collagen based matrix structure removed from a submucosa tissue source. These features and other features disclosed in U.S. Pat. No. 6,206,931 could be used with the present invention, and the disclosure of U.S. Pat. No. 6,206,931 is herein incorporated by reference.

PCT Patent Publication Number No. WO99/29262 entitled "Endoluminal Aortic Stents" discloses a fenestrated prosthesis for placement where there are intersecting arteries. This feature and other features disclosed in PCT Patent Publication Number No. WO99/29262 could be used with the present invention, and the disclosure of PCT Patent Publication Number No. WO99/29262 is herein incorporated by reference.

PCT Patent Publication Number No. WO03/034948 entitled "Prostheses for Curved Lumens" discloses prostheses with arrangements for bending the prosthesis for placement into curved lumens. This feature and other features disclosed in PCT Patent Publication Number No. WO03/034948 could be used with the present invention, and the disclosure of PCT Patent Publication Number No. WO03/034948 is herein incorporated by reference.

United States Published Patent Application No. 20030233140 entitled "Trigger Wire System" discloses release wire systems for the release of stent grafts retained on introducer devices. This feature and other features disclosed in United States Published Patent Application No. 20030233140 could be used with the present invention, and the disclosure of United States Published Patent Application No. 20030233140 is herein incorporated by reference.

United States Published Patent Application No. 20040098079 entitled "Thoracic Aortic Stent Graft Deployment Device" discloses introducer devices adapted for deployment of stent grafts particularly in the thoracic arch. This feature and other features disclosed in United States Published Patent Application No. 20040098079 could be used with the present invention and the disclosure of United States Published Patent Application No. 20040098079 is herein incorporated by reference.

United States Published Patent Application No. 20040054396 entitled "Stent-Graft Fastening" discloses arrangements for fastening stents onto grafts particularly for exposed stents. This feature and other features disclosed in United States Published Patent Application No. 20040054396 could be used with the present invention, and the disclosure of United States Published Patent Application No. 20040054396 is herein incorporated by reference.

PCT Patent Publication Number No. WO03/053287 entitled "Stent Graft with Improved Graft Adhesion" discloses arrangements on stent grafts for enhancing the adhesion of such stent grafts into walls of vessels in which they are deployed. This feature and other features disclosed in PCT Patent Publication Number No. WO03/053287 could be used with the present invention, and the disclosure of PCT Patent Publication Number No. WO03/053287 is herein incorporated by reference.

PCT Patent Publication Number No. WO98/53761 entitled "A Prosthesis and a Method and Means of Deploying a Prosthesis", which is herein incorporated by reference, discloses various embodiments of an introducer for positioning an expandable endovascular prosthesis in a lumen of a patient. In one disclosed embodiment, the introducer includes a trigger wire mechanism to control the release of a proximal portion of the prosthesis. It would be desirable to provide a method and apparatus to deploy a graft prosthesis that provides a controlled release of a proximal portion of the prosthesis without the need for a trigger wire.

SUMMARY

An introducer for an expandable, endovascular prosthesis with a self expanding stent has proximal and distal prosthesis positioning mechanisms. The proximal prosthesis positioning mechanism has a cylindrical sleeve and a first control member to selectively disengage the cylindrical sleeve from the prosthesis. The distal prosthesis positioning mechanism has a distal retention section and a second control member to selectively disengage the distal retention section from the prosthesis. The first control member includes a first region coupled to the distal prosthesis positioning mechanism that extends longitudinally therefrom. The first control member also includes a second region that is coupled to the first region. The second region selectively and proximally disengages the self expanding stent to retain the self expanding stent in the cylindrical sleeve.

A method of placing a prosthesis into an internal lumen with an insertion assembly includes a step of inserting the insertion assembly including the prosthesis into the internal lumen and withdrawing a sheath from the insertion assembly to expose the prosthesis. A force is exerted on the prosthesis in a proximal direction by a release mechanism to retain the prosthesis in a prosthesis retention mechanism of the insertion assembly. The prosthesis retention mechanism is moved proximally away from the release mechanism to release the prosthesis from the insertion assembly. The sheath is replaced onto the insertion assembly, and the insertion assembly is retracted.

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

Figure 1:
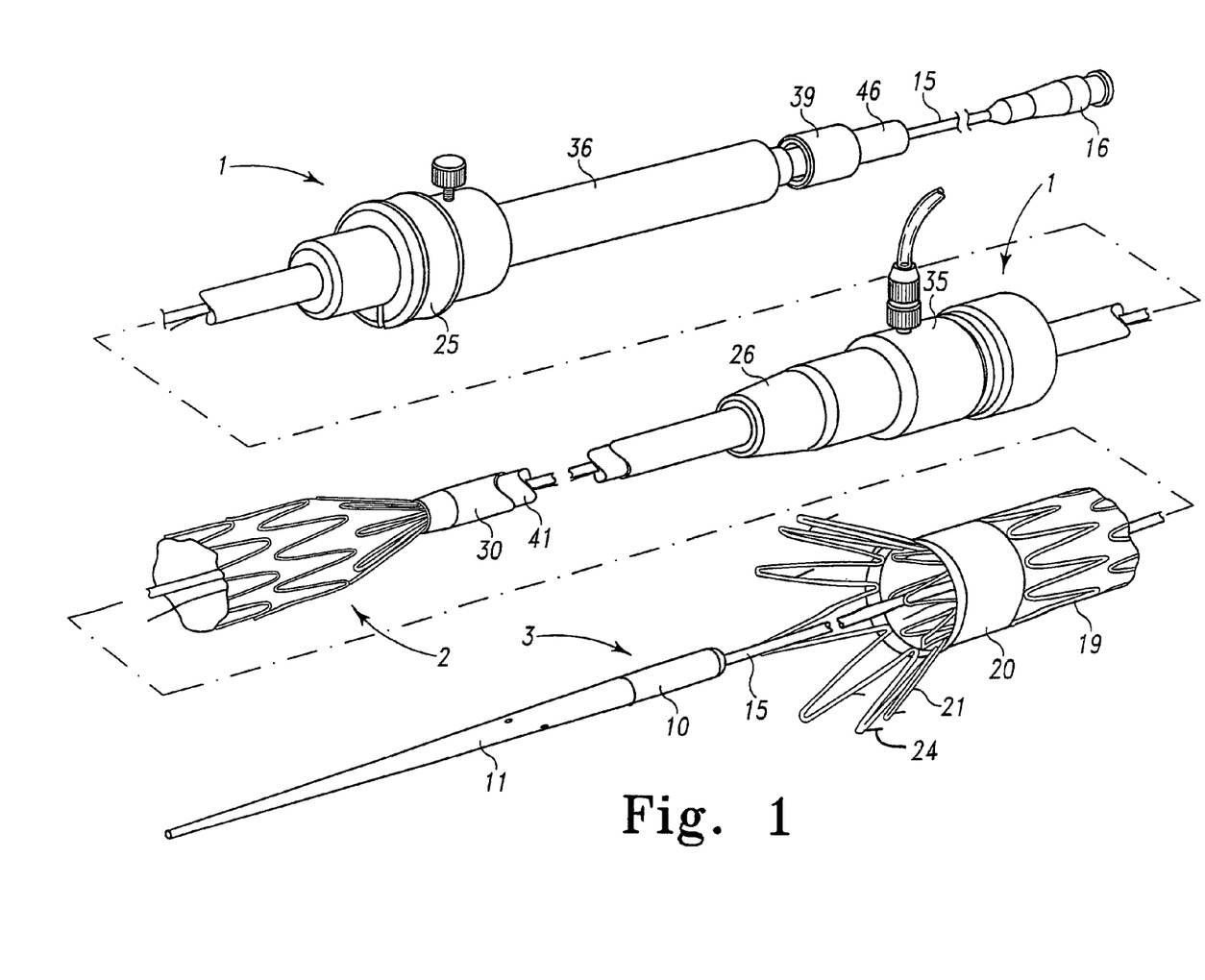
FIG. 1 is a perspective view of an introducer with a prosthesis partially deployed.

FIG. 1 shows a prosthesis 20, and an endovascular deployment system, also known as an introducer, for deploying the prosthesis 20 in a lumen of a patient during a medical procedure. The introducer includes an external manipulation section 1, a distal positioning mechanism and attachment region 2, and a proximal positioning mechanism and attachment region 3. During a medical procedure to deploy the prosthesis 20, the distal and proximal attachment regions 2 and 3 will travel through the lumen within a patient to a desired deployment site. The external manipulation section 1, which is acted upon by a user to manipulate the introducer, remains outside of the patient throughout the procedure.

The prosthesis 20 comprises a tubular graft material, such as Dacron, with self expanding stents 19 attached thereto. The self expanding stents 19 cause the prosthesis 20 to expand following disengagement from the introducer. The prosthesis 20 also includes a self expanding zigzag stent 21 that extends from the prosthesis proximal end. When disengaged from the introducer, the self expanding zigzag stent 21 anchors the proximal end of the prosthesis 20 to the lumen.

Figure 3:
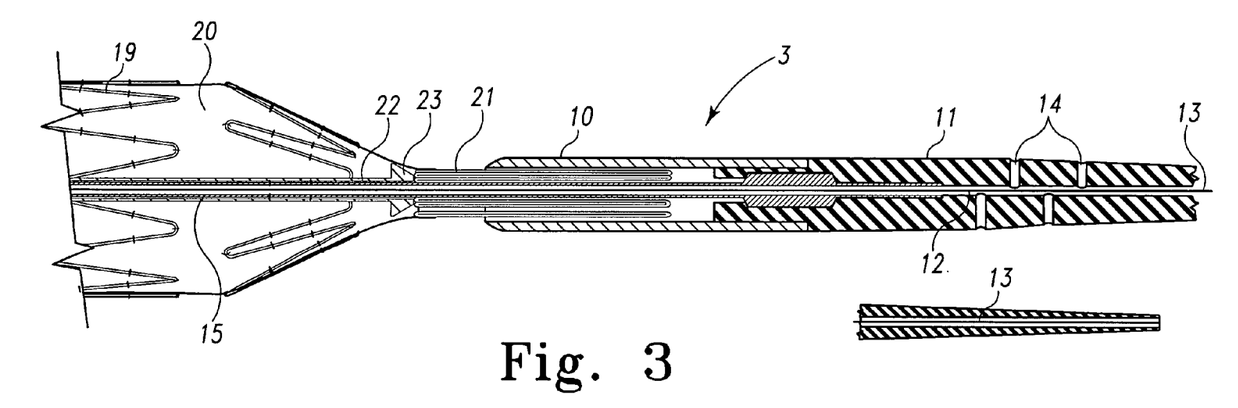
FIG. 3 is a sectional detail view of a portion of the introducer around the proximal end of the prosthesis.

FIG. 3 shows the proximal attachment region 3 in greater detail. The proximal attachment region 3 includes a cylindrical sleeve 10. The cylindrical sleeve 10 has a long tapered flexible extension 11 extending from the sleeve proximal end. The flexible extension 11 has an internal longitudinal aperture 12. The longitudinal aperture 12 facilitates advancement of the tapered flexible extension 11 along an insertion wire 13. The aperture 12 also provides a channel for the introduction of medical reagents. For example, it may be desirable to supply a contrast agent to allow angiography to be performed during placement and deployment phases of the medical procedure.

A thin walled tube 15, which can be made of metal, is fastened to the extension 11. The thin walled tube 15 is flexible so that the introducer can be advanced along a relatively tortuous vessel, such as a femoral artery. The flexibility of the thin walled tube 15 allows manipulation longitudinally and rotationally of the proximal attachment region 3. The thin walled tube 15 extends through the introducer to the manipulation section 1, terminating at a connection means 16, as shown in FIG. 6.

Figure 6:
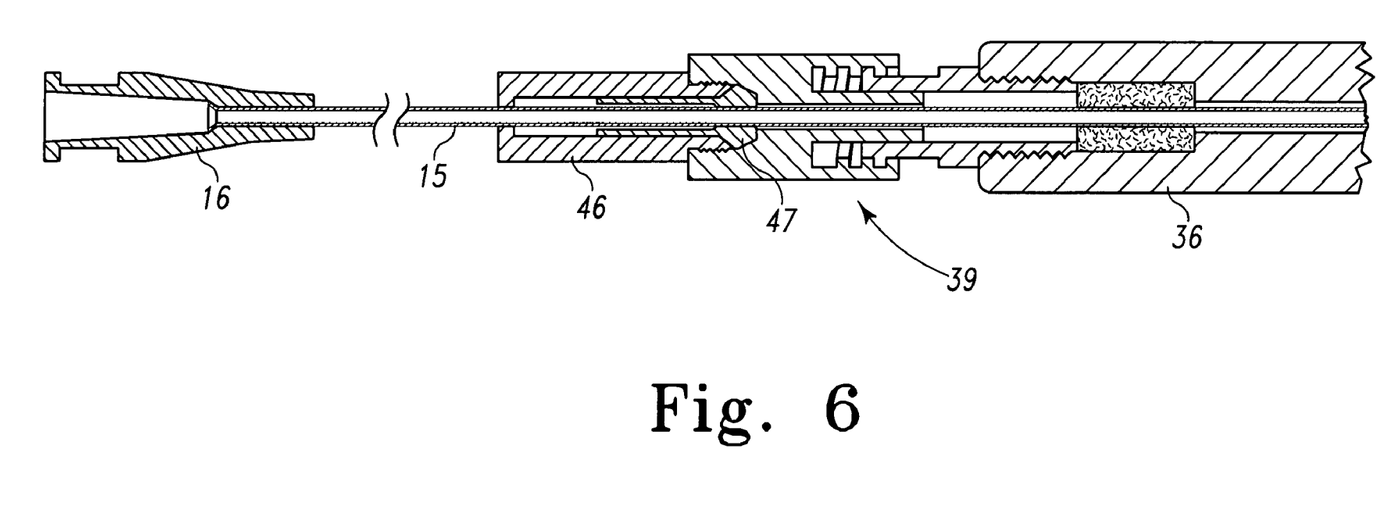
FIG. 6 is a sectional detail view of the introducer around the pin vise clamp and the medical reagent introduction tube.

Regarding the introduction of reagents, FIG. 6 shows that the connection means 16 is adapted to accept a syringe to facilitate the introduction of reagents into the thin walled tube 15. The thin walled tube 15 is in fluid communication with the aperture 12 of the flexible extension 11. Therefore, reagents introduced into connection means 16 can flow through the aperture 12 and emanate from the apertures 14.

Figure 2:
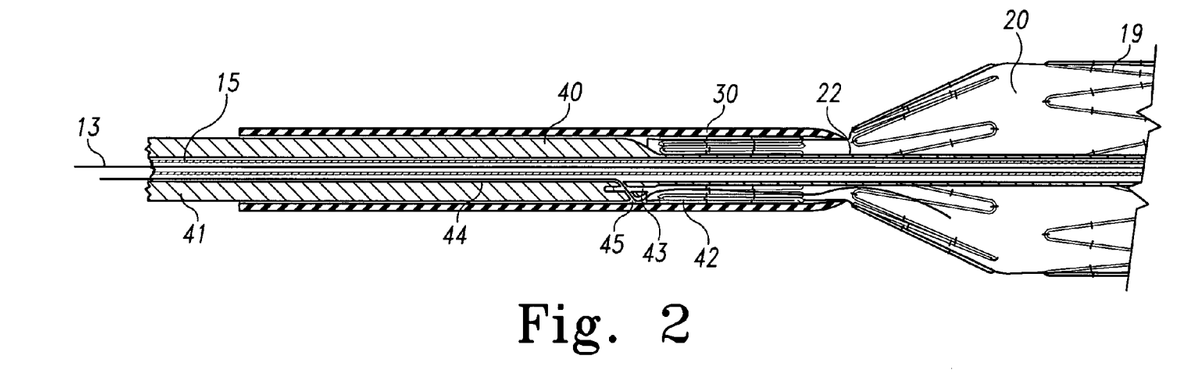
FIG. 2 is a sectional detail view of a portion of the introducer around the distal end of the prosthesis.

As shown in FIG. 2, a tube 41, which can be made of a suitable plastic, is coaxial and radially outside the thin walled tube 15. The tube 41 is "thick walled", that is to say the thickness of the wall of tube 41 is several times that of the thin walled tube 15. A sheath 30 is coaxial and radially outside the thick walled tube 41. The thick walled tube 41 and the sheath 30 extend distally to the manipulation region 1, as shown in FIG. 4.

FIGS. 2 and 3 illustrate retention, and distal and proximal release mechanisms of the introducer, respectively. During the placement phase of the medical procedure, the prosthesis 20 can be retained in a compressed condition by the sheath 30.

Figure 4:
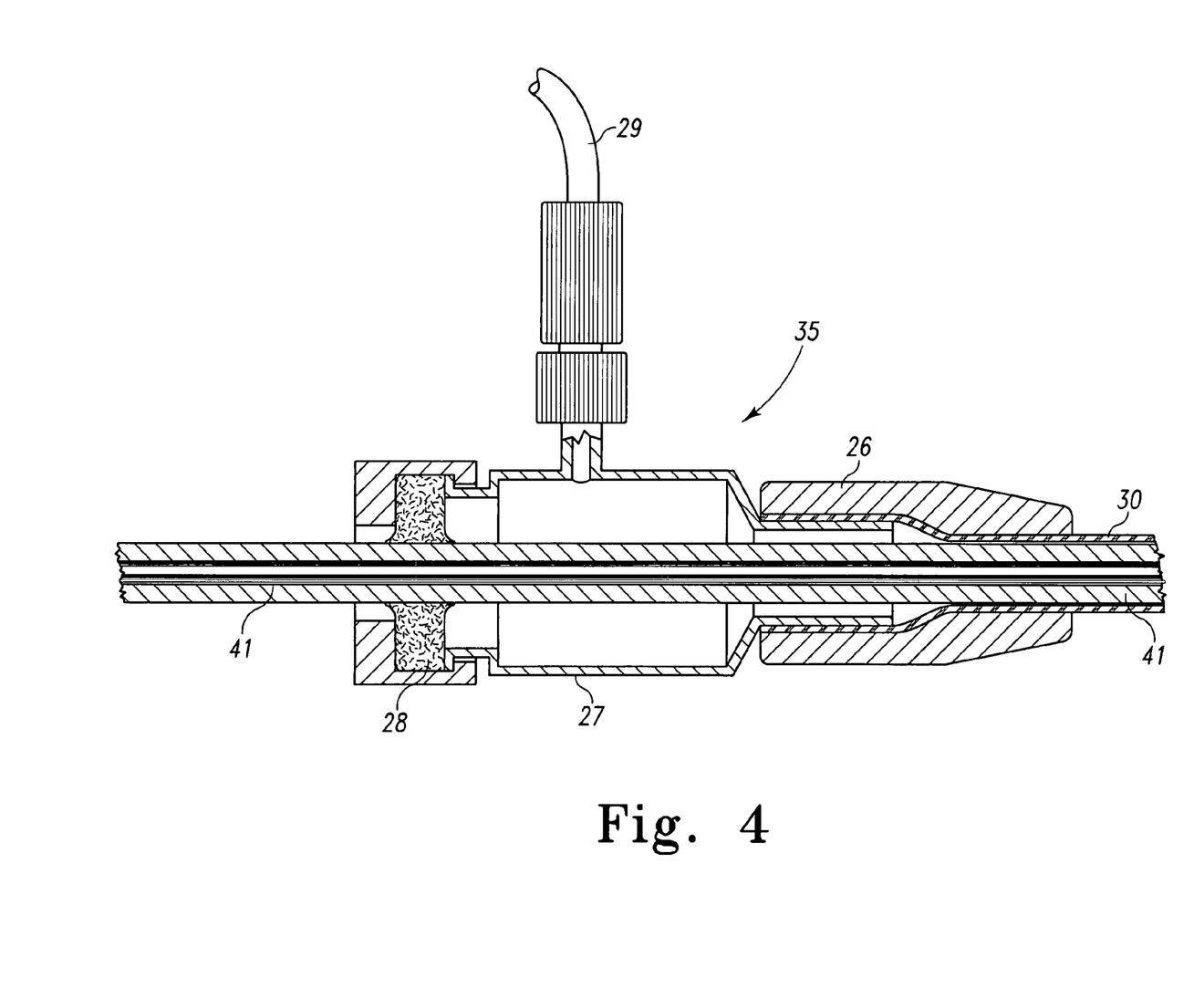
FIG. 4 is a sectional detail view of a portion of the introducer around the haemostatic seal.

The sheath 30 extends distally to a gripping and haemostatic sealing means 35 of the external manipulation section 1, shown in FIG. 4.

During assembly of the introducer, the sheath 30 can be advanced over the cylindrical sleeve 10 of the proximal attachment region 3 while the prosthesis 20 is held in a compressed state by an external force. A distal attachment (retention) section 40 is formed in the thick walled tube 41 to retain the distal end of the prosthesis 20. Alternatively, the distal attachment section 40 can be a separate piece coupled to the thick walled tube 41.

A thin walled cannula 22 is also formed in the thick walled tube 41. Alternatively, the thin walled cannula 22 can be a separate piece coupled to the thick walled tube 41. The thin walled cannula 22 extends from the distal attachment section 40 to a conical tip 23. The conical tip 23 can be either coupled to the end of the thin walled cannula 22 or formed in the thick walled tube 41. The thick walled tube 41, the thin walled cannula 22, and the conical tip 23 are each coaxial with and radially outside the thin walled tube 15.

When the prosthesis 20 is in a compressed condition, the self expanding zigzag stent 21 is retained in the cylindrical sleeve 10 by the conical tip 23. The conical tip 23 asserts pressure on the distal end of the self expanding stent 21 in the proximal direction, holding the self expanding zigzag stent 21 in the cylindrical sleeve 10 without the need for a trigger wire. The self expanding stent 21 is disengaged by first retracting the sheath 30, and then sliding the proximal attachment region 3, including the cylindrical sleeve 10, away from the conical tip 23. Once the cylindrical sleeve 10 has cleared the self expanding stent 21, the stent 21 will expand. The thin walled cannula 22 and the conical tip 23 form a control member to selectively disengage the cylindrical sleeve 10 from the prosthesis 20 by exerting force on (pushing) the self expanding stent 21 into the cylindrical sleeve 10 until the prosthesis 20 is positioned at a desired site in the lumen.

Figure 5:
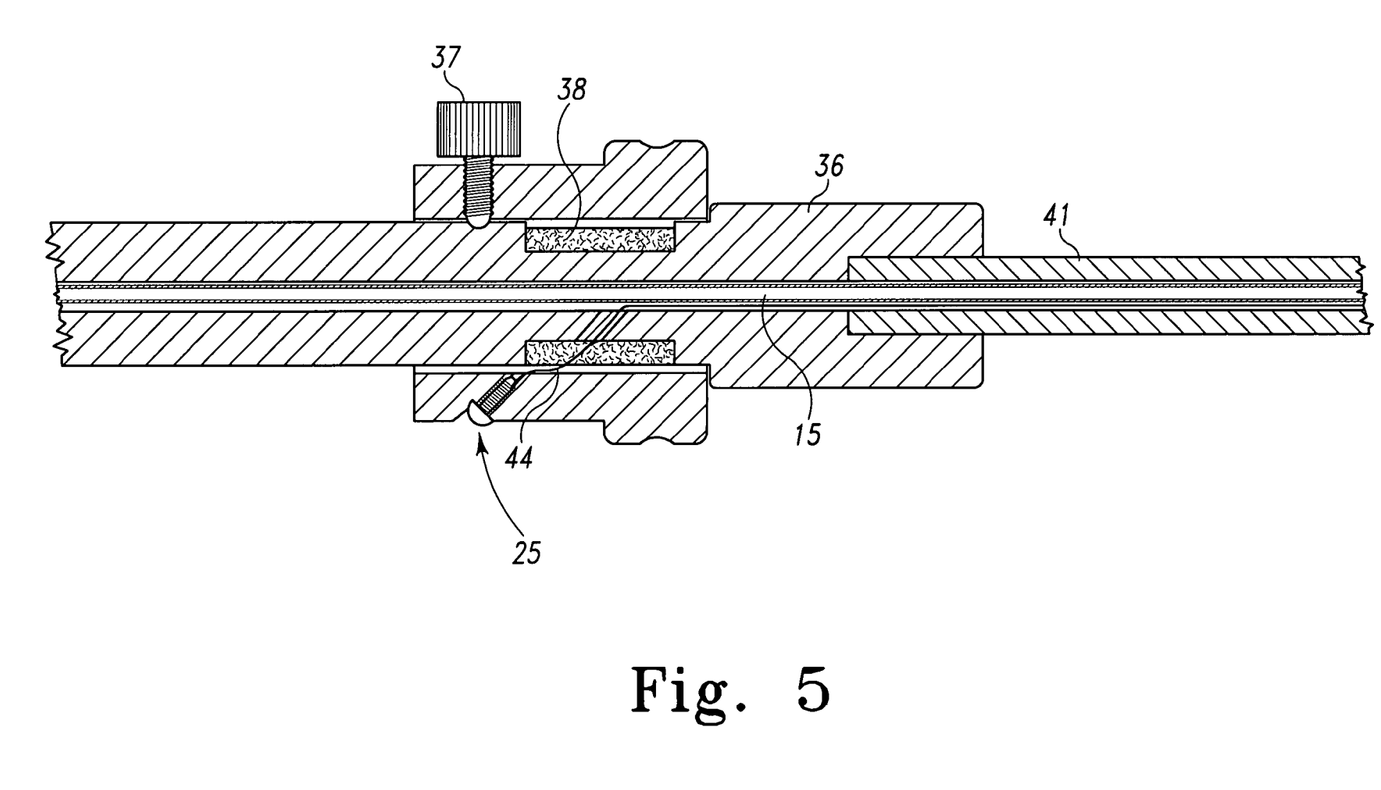
FIG. 5 is a sectional detail view of a portion of the introducer around the trigger wire release mechanism.

The distal end 42 of the prosthesis 20 is retained by the distal attachment section 40 of the thick walled tube 41. The distal end 42 of the prosthesis 20 has a loop 43 through which a distal trigger wire 44 extends. The distal trigger wire 44 extends through an aperture 45 in the distal attachment section 40 into the annular region between the thin walled tube 15 and the thick walled tube 41. As shown in FIG. 5, the distal trigger wire 44 extends through the annular space between the thick walled tube 41 and the thin walled tube 15 to the manipulation region 1. The distal trigger wire 44 exits the annular space at a distal wire release mechanism 25. The distal trigger wire 44 and the distal wire release mechanism 25 form a control member to selectively disengage the distal retention section 40 from the prosthesis 20 when it is positioned at a desired site in a lumen of a patient.

FIG. 4 shows the haemostatic sealing means 35 of the external manipulation section 1 shown in greater detail. The haemostatic sealing means 35 includes a haemostatic seal 27 a side tube 29. The haemostatic seal 27 includes a clamping collar 26 that clamps the sheath 30 to the haemostatic seal 27. The haemostatic seal 27 also includes a seal ring 28, which can be made of silicone. The seal ring 28 forms a haemostatic seal around the thick walled tube 41. The side tube 29 facilitates the introduction of medical reagents between the thick walled tube 41 and the sheath 30.

FIG. 5 shows a proximal portion of the external manipulation section 1. The release wire actuation section has a body 36 that is mounted onto the thick walled tube 41. The thin walled tube 15 passes through the body 36. The distal wire release mechanism 25 is mounted for slidable movement on the body 36. A clamping screw 37 prevents inadvertent early disengagement of the distal end 42 of the prosthesis 20. A haemostatic seal 38 is provided so the trigger wire 44 can extend out through the body 36 to the release mechanism 25 without unnecessary blood loss during the medical procedure.

FIG. 6 shows a distal portion of the external manipulation section 1. A pin vise 39 is mounted onto the distal end of the body 36. The pin vise 39 has a screw cap 46. When screwed in, the vise jaws 47 clamp against and engage the thin walled tube 15. When the vise jaws 47 are engaged, the thin walled tube 15 can only move with the body 36, and hence the thin walled tube 15 can only move with the thick walled tube 41. With the screw cap 46 tightened, the entire assembly, except for the external sheath 30, can be moved as one.

FIGS. 7 through 12 show the various stages of the deployment of the prosthesis 20 during the medical procedure. A guide wire 13 is introduced into a lumen such as the femoral artery and advanced until its tip is beyond the region into which the prosthesis 20 is to be deployed.

Figure 7:
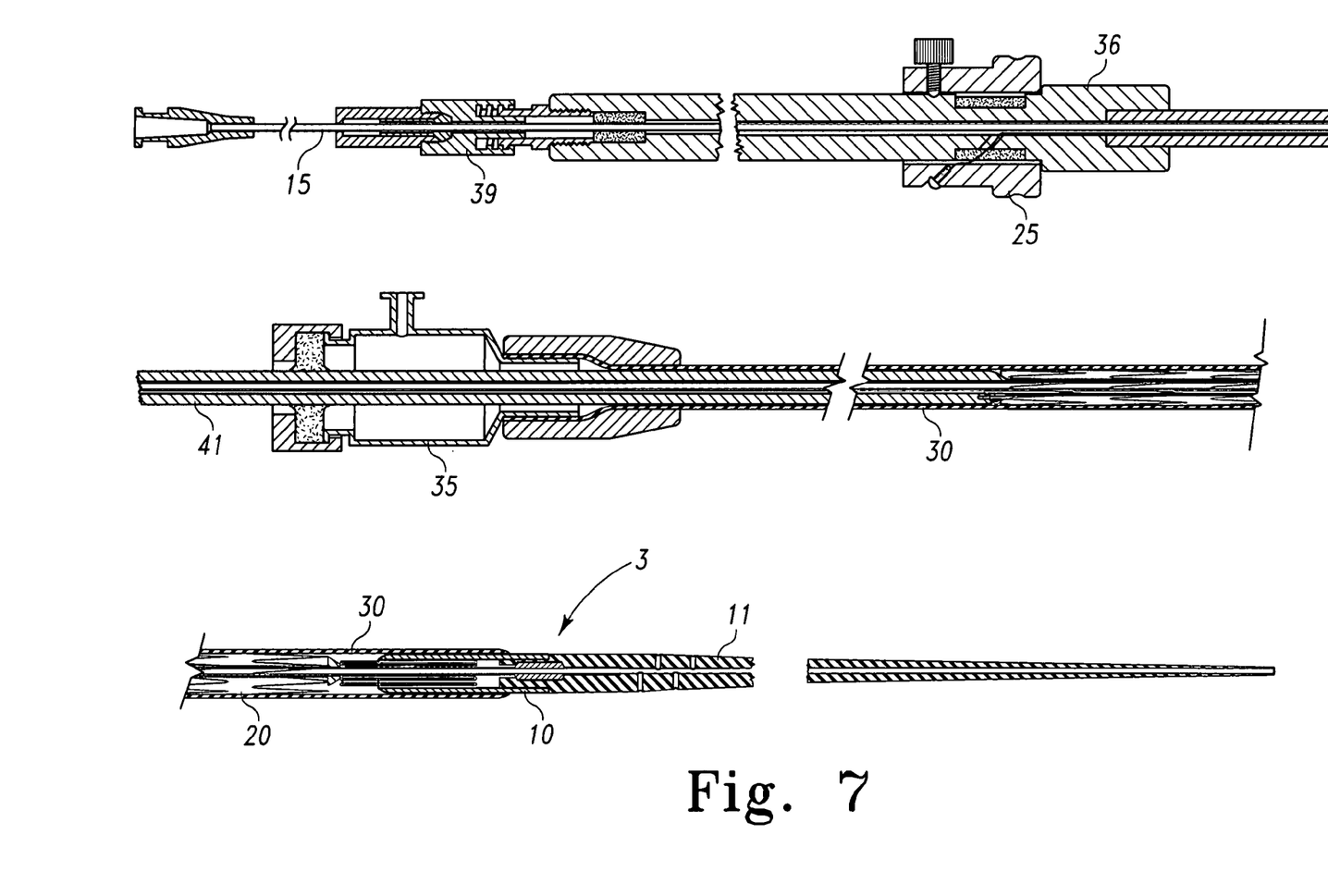
FIG. 7 is a sectional view of the introducer of FIG. 1 fully loaded and ready for introduction into a patient.

In FIG. 7, the introducer assembly is shown fully assembled ready for introduction into a patient. The prosthesis 20 is retained at each of its ends by the proximal and distal retaining assemblies respectively, and compressed by the external sheath 30. If it is an aortic aneurism which is to be grafted, the introducer assembly can be inserted through a femoral artery over the guide wire 13 in the form as shown in FIG. 7, and positioned by well-known radiographic techniques (not discussed here).

Figure 8:
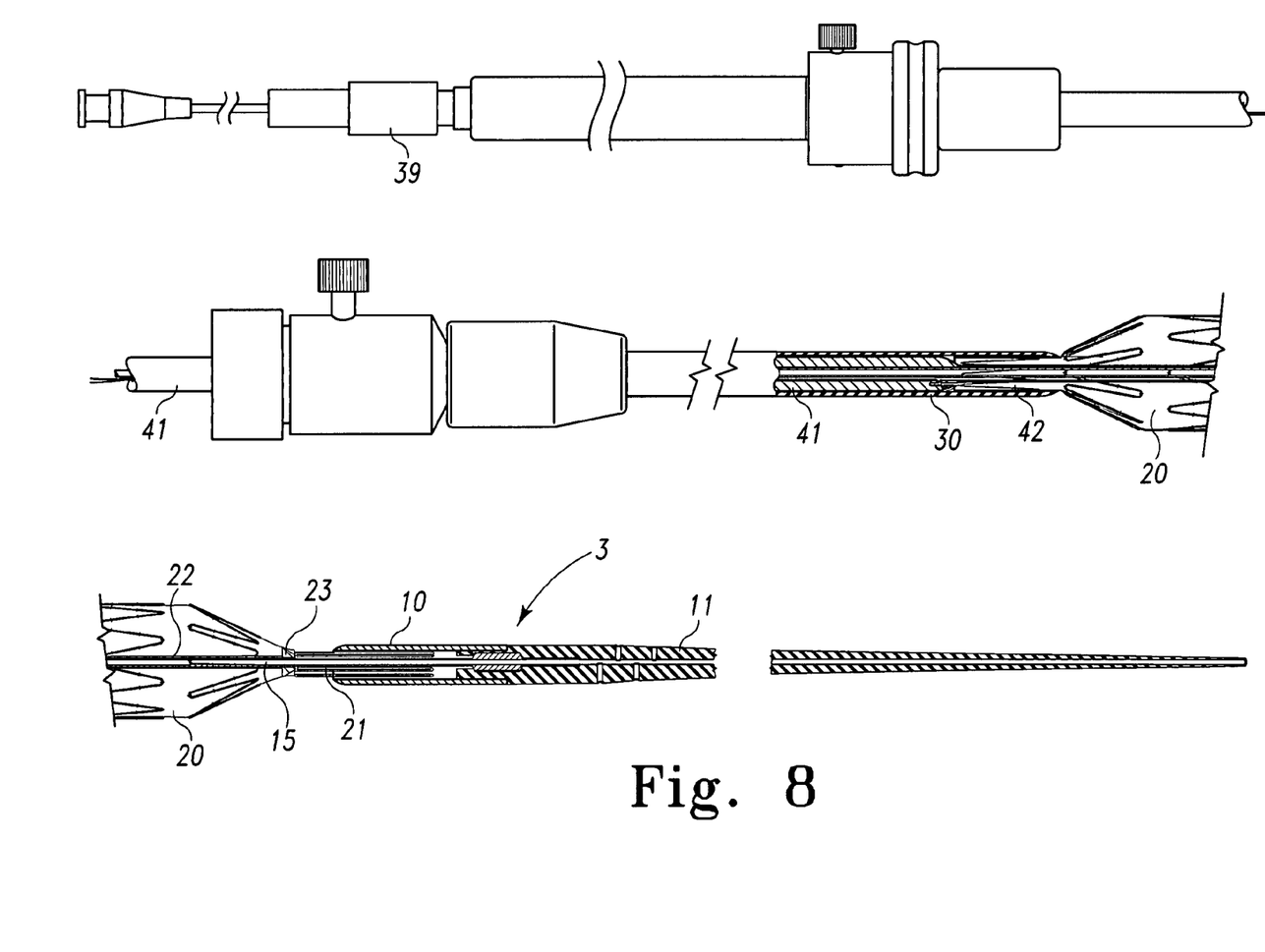
FIG. 8 is a side elevation view, partially in section, of the introducer of FIG. 7 in a first stage of deployment of the prosthesis.

In FIG. 8, the introducer assembly is in a desired position for deployment of the prosthesis 20. The external sheath 30 is withdrawn to just proximal of the distal attachment section 40. This action disengages the middle portion of the prosthesis 20 so that it can expand radially. The proximal self expanding stent 21, however, is still retained within the cylindrical sleeve 10. Also, the distal end 42 of the prosthesis 20 is still retained within the external sheath 30.

By release of the pin vise 39 to allow small movements of the thin walled tube 15 with respect to the thick walled tube 41, the prosthesis 20 can be lengthened or shortened or rotated or compressed for accurate placement in the desired location within the lumen. X-ray opaque markers (not shown) can be placed along the prosthesis 20 to assist with placement of the prosthesis.

Figure 9:
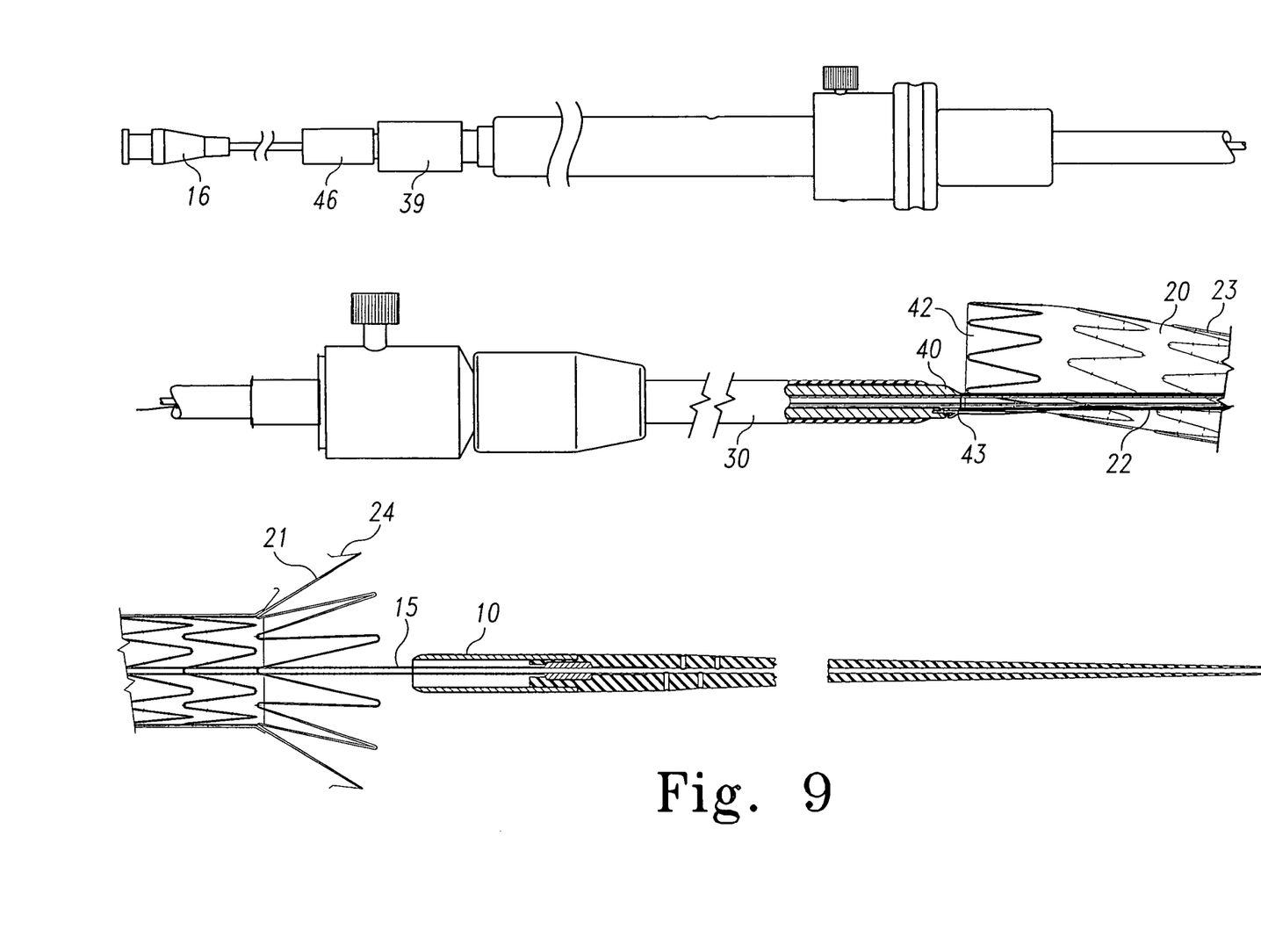
FIG. 9 is a side elevation view, partially in section, of the introducer of FIG. 7 at the release of the proximal end stage of deployment.

In FIG. 9, the screw cap 46 of the pin vise 39 has been loosened so that the thin walled tube 15 can been pushed in a proximal direction to move the proximal attachment sleeve 10 in a proximal direction. When the proximal attachment sleeve 10 no longer surrounds the self expanding stent 21 at the proximal end of the prosthesis 20, the self expanding stent 21 expands. When the stent 21 expands, the hooks or barbs 24 on the self expanding stent 21 grip into the walls of the lumen of the patient to hold the proximal end of the prosthesis 20 in place.

At this point, the distal end 42 of the prosthesis 20 is still retained by the distal attachment section 40, with the loop 43 retained therein. The external sheath 30 has been withdrawn to a position distal of the distal attachment section 40 to allow the distal end 42 of the prosthesis 20 to expand. At this point, the distal end 42 of the prosthesis 20 can still be moved. Consequently, the prosthesis 20 can still be rotated or lengthened or shortened or otherwise moved to for accurate positioning. Where the prosthesis 20 to be deployed is a bifurcated graft, the movement at this stage may ensure that the shorter leg is directed in the direction of the contra-iliac artery.

Figure 10:
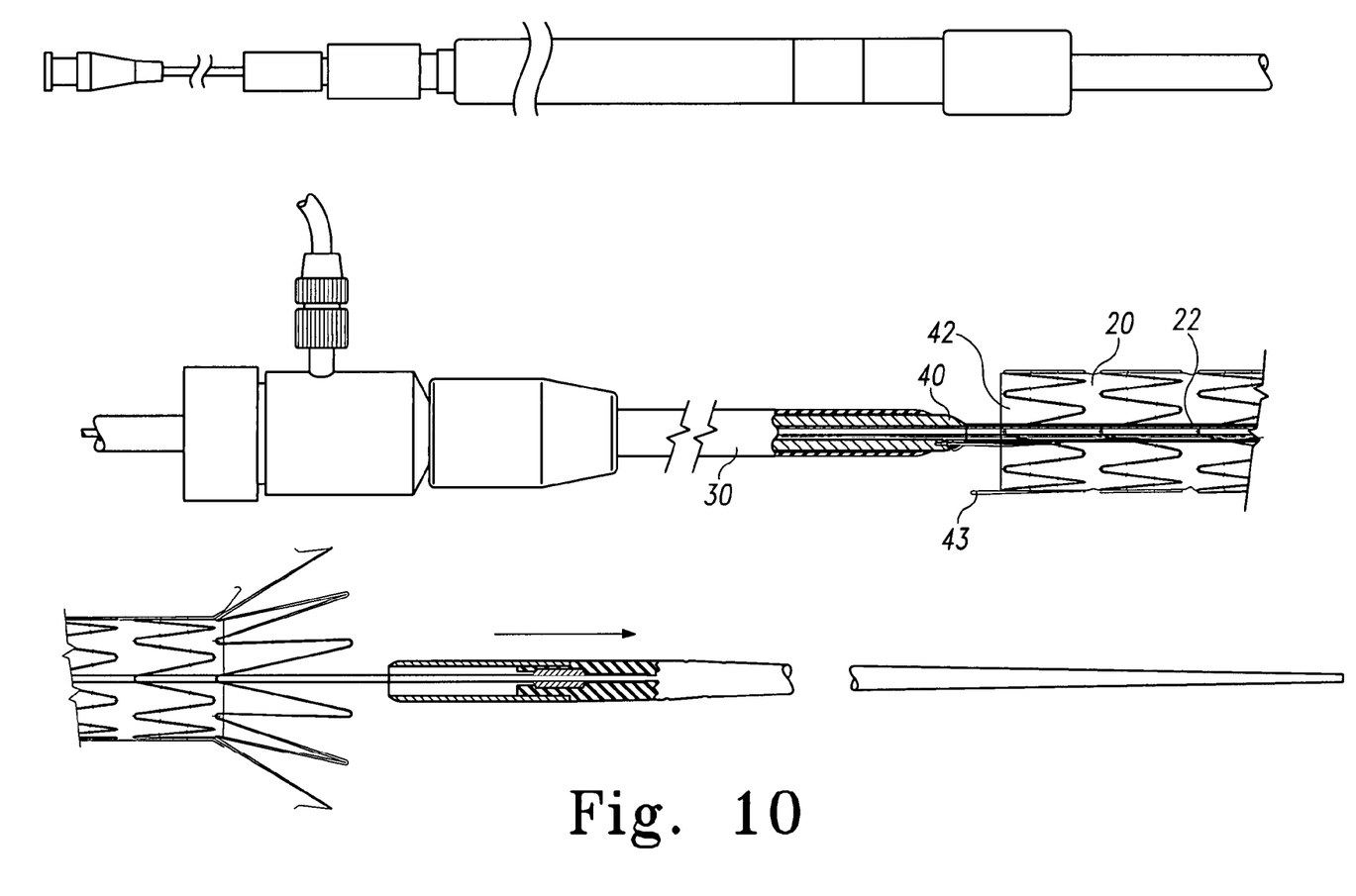
FIG. 10 is a side elevation view, partially in section, of the introducer of FIG. 7 at the release of the distal end stage of deployment.

In FIG. 10, the distal end 42 of the prosthesis 20 has been disengaged by removal of the distal trigger wire 44. At this stage, the distal trigger wire release mechanism 25 and the distal trigger wire 44 can be removed completely. This removal can be accomplished by passing the distal wire release mechanism 25 over the pin vise 39 and the connection means 16. The loop 43 of the terminal distal self expanding zigzag stent 19 is thus disengaged, and the prosthesis 20 is now free to expand to the walls of the vessel. At this point, the introducer is ready to be removed.

Figure 11:
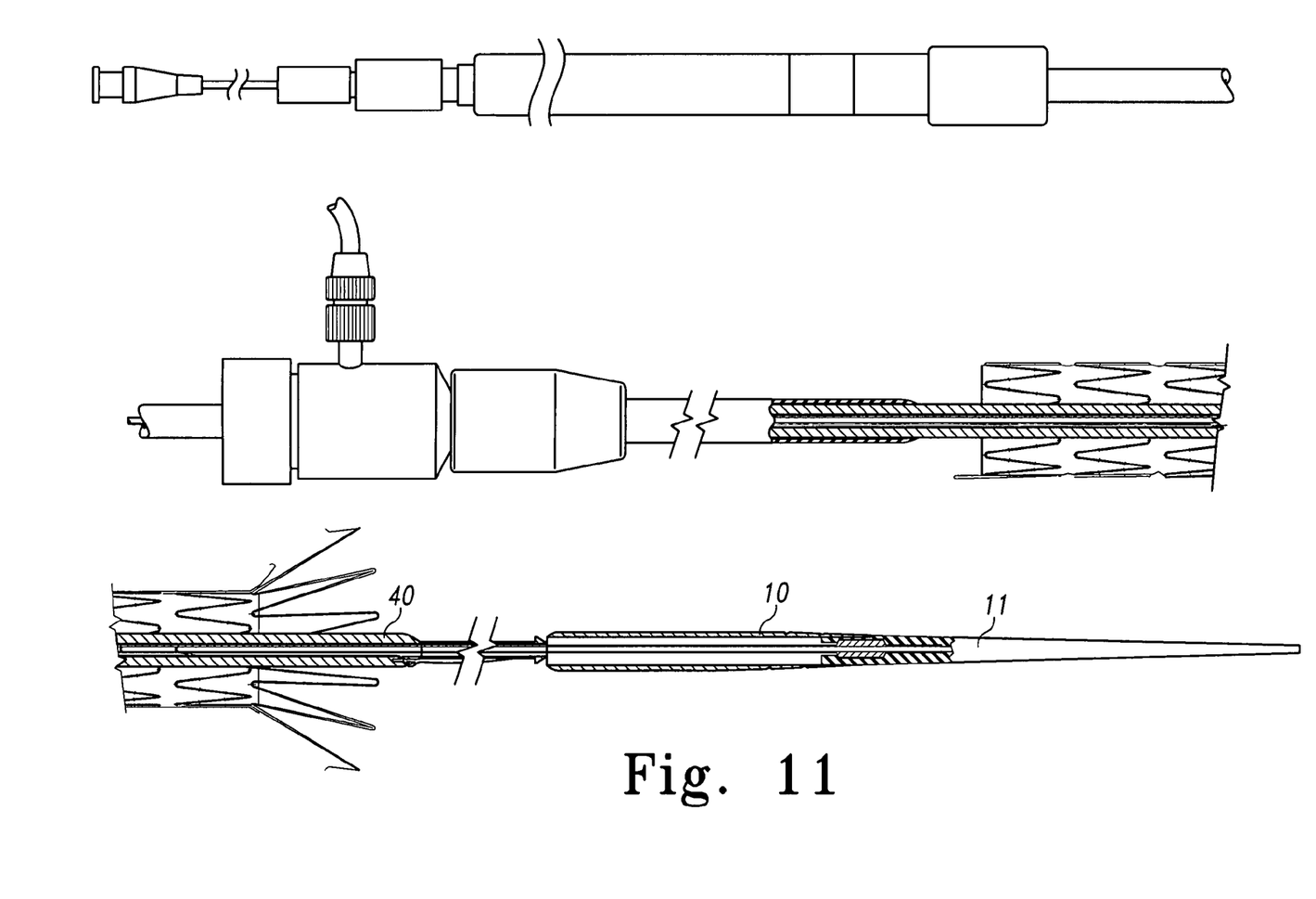
FIG. 11 is a side elevation view, partially in section, of the introducer of FIG. 7 showing an advancement of the distal attachment mechanism to the proximal attachment mechanism.

In FIG. 11, the first stage of removal is shown. First, the distal attachment section 40 is advanced until the conical tip 23 is received in the rear of the proximal attachment sleeve 10. Next, the proximal attachment sleeve 10, the tapered flexible extension 11, and the distal attachment section 40, including the thin walled cannula 22 and the conical tip 23, are removed together, as shown in FIG. 12.

Figure 12:
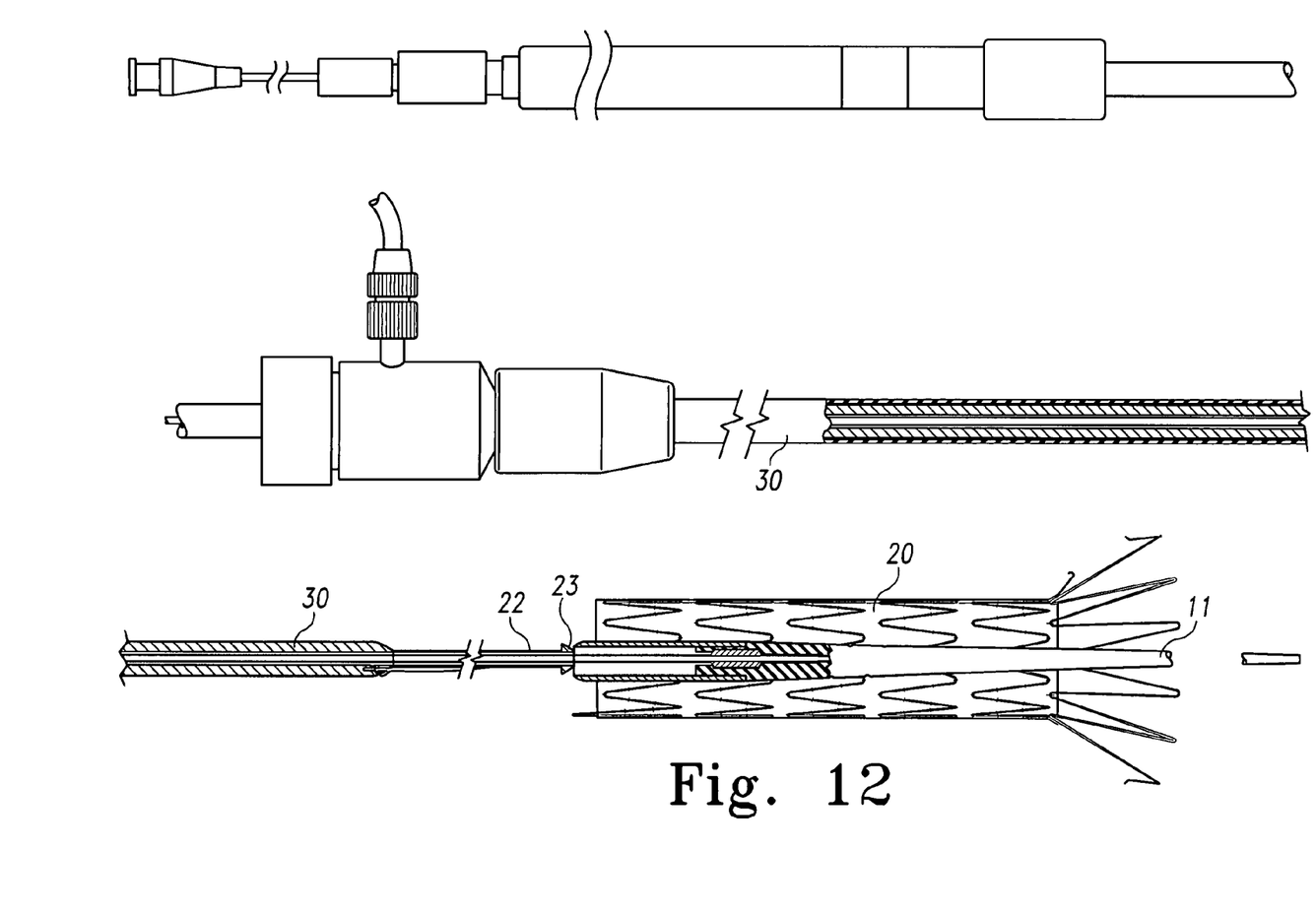
FIG. 12 is a side elevation view, partially in section, of the introducer of FIG. 7 showing the withdrawal of the introducer from within the expanded prosthesis.

In FIG. 12, the sheath 30 has been advanced to cover the join between the proximal attachment sleeve 10 and the distal attachment section 40. The sheath 30 can be removed with the proximal attachment sleeve 10, the tapered flexible extension 11 and the distal attachment section 40. Alternatively, these items could be removed separately, followed by removal of the external sheath 30.

Throughout this specification, unless the context requires otherwise, the words "comprise" and "include" and variations such as "comprising" and "including" will be understood to imply the inclusion of an item or group of items, but not the exclusion of any other item or group items.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together. Accordingly, the invention is not to be restricted except in light of the attached claims and their equivalents.

The invention claimed is:

1. An introducer for an expandable endovascular prosthesis having a tubular member defining a lumen about a longitudinal axis, including a proximal portion, a distal portion, and a middle portion between the proximal and distal portions, the prosthesis being radially movable between a compressed configuration and an expanded configuration, the introducer comprising:

a distal prosthesis positioning mechanism including a distal retention section positioned radially inside of a sheath to retain said prosthesis distal portion until deployment, and a first control member to selectively disengage the distal retention section from said prosthesis distal portion;

a proximal prosthesis positioning mechanism including a cylindrical sleeve to maintain the proximal portion of said prosthesis in the compressed configuration until deployment, the cylindrical sleeve having a tapered extension coupled thereto and extending proximally therefrom, and a second control member to selectively disengage said prosthesis proximal portion from the cylindrical sleeve, wherein the second control member includes a first region coupled to the distal prosthesis positioning mechanism extending longitudinally therefrom, and a second region including an enlarged uninflatable tip coupled to the first region, the enlarged tip comprising a conical surface facing the proximal direction, the enlarged tip positioned within said prosthesis lumen, the conical surface selectively abutting a distal end of said prosthesis proximal portion to retain said prosthesis proximal portion in the cylindrical sleeve; and the sheath positioned radially outside of the cylindrical sleeve to retain the distal and middle portions of said prosthesis in the compressed configuration until deployment.

2. The introducer of claim 1 further comprising a third control member attached to the tapered extension of the cylindrical sleeve, wherein the third control member is slidably engaged with the second control member to selectively disengage the cylindrical sleeve from said prosthesis by proximal movement of the third control member and the cylindrical sleeve away from said prosthesis.

3. The introducer of claim 2 further comprising a first control arrangement to control a length, an axial position and an angular position of said prosthesis distal portion at a desired site in a body vessel lumen by selective engagement of the first control member of the distal retention section with said prosthesis distal portion while retaining the second control member of said prosthesis proximal portion in the cylindrical sleeve.

4. The introducer of claim 2 further comprising a second control arrangement to control a length, an axial position and an angular position of said prosthesis proximal portion at a desired site in a body vessel lumen by selective movement of the third control member.

5. The introducer of claim 2, wherein the first region and the second region of the second control member includes a first tube, the enlarged tip is coupled to a proximal end of the first tube, and wherein the third control member includes a second tube disposed radially inward from the first tube and slidably engaged therewith, the second tube having a portion extending past the proximal end of the first tube.

6. The introducer of claim 1, wherein only the abutting relationship between the conical surface of the enlarged tip and the distal end of said prosthesis proximal portion retains said prosthesis proximal portion in the cylindrical sleeve.

7. The introducer of claim 1, wherein the sheath disengages from the cylindrical sleeve by distal movement to permit the middle portion of said prosthesis to radially move to the expanded configuration, the sheath moving to a location to maintain said prosthesis distal portion in the compressed configuration while the cylindrical sleeve maintains said prosthesis proximal portion in the compressed configuration.

8. The introducer of claim 1, wherein the middle portion of said prosthesis radially moves to the expanded configuration while the cylindrical sleeve maintains said prosthesis proximal portion in the compressed configuration and the sheath maintains said prosthesis distal portion in the compressed configuration.

9. The introducer of claim 1, wherein the first region comprises a tube.

10. The introducer of claim 9, wherein the second region comprises a tube coupled to and extending proximally from the first region tube, the second region tube having a proximal end, where the enlarged tip is disposed at the proximal end of the second region tube.

11. The introducer of claim 9, wherein the enlarged tip is longitudinally spaced from the cylindrical sleeve in the distal direction.

12. The introducer of claim 1, wherein the enlarged tip of the second region further comprises a base perpendicular to the longitudinal axis, the base facing toward the distal retention section.

13. The introducer of claim 12, wherein the first region and the second region including the enlarged tip having the conical surface are formed from a single tube.

14. An introducer for an expandable endovascular prosthesis having a tubular member defining a lumen about a longitudinal axis, including a distal portion, a proximal portion having a self-expanding stent at a proximal end of said prosthesis proximal portion, and a middle portion between the proximal and distal portions, the prosthesis being radially movable between a compressed configuration and an expanded configuration, the introducer comprising:

a control section to be maintained external to a patient;

a sheath positioned radially outside of said prosthesis and contactable therewith to retain the distal and middle portions of said prosthesis in the compressed configuration;

a cylindrical sleeve positioned radially inside of the sheath to maintain the self-expanding stent of said prosthesis in the compressed configuration; and a control member including a first region coupled to the control section extending longitudinally therefrom, and a second region coupled to the first region including an uninflatable conical tip positioned within said prosthesis lumen between the prosthesis distal portion and the self-expanding stent, the conical tip having a conical surface facing the proximal direction, the conical surface abutting a distal end of the self expanding stent to retain the self expanding stent within the cylindrical sleeve until said prosthesis is positioned at a desired site within a body vessel lumen of the patient.

15. The introducer of claim 14, wherein the control member is a first control member and the cylindrical sleeve has a tapered extension coupled thereto and extending proximally therefrom, and the introducer further comprises a second control member attached to tapered extension of the cylindrical sleeve, wherein the second control member is slidably engaged with the first control member to selectively disengage the cylindrical sleeve from the self expanding stent by proximal movement of the cylindrical sleeve away from the self expanding stent.

16. The introducer of claim 15 further comprising a first control arrangement to control a length, an axial position and an angular position of said prosthesis distal portion at a desired site in a body vessel lumen by selective engagement of the first control member of the distal retention section with said prosthesis distal portion while retaining the second control member of said prosthesis proximal portion in the cylindrical sleeve.

17. The introducer of claim 15 further comprising a second control arrangement to control a length, an axial position and an angular position of said prosthesis proximal portion at a desired site in a body vessel lumen by selective movement of the third control member.

18. The introducer of claim 15, wherein the first region comprises a tube and the second region comprises a tube coupled to and longitudinally extending from the first region tube, the conical tip being coupled to the second region tube, and wherein the second control member includes a tube disposed radially inward from the tubes of both of the first and second regions and slidably engaged therewith.

19. The introducer of claim 14, wherein the sheath disengages from the cylindrical sleeve by distal movement of the sheath to permit the middle portion of said prosthesis to radially move to the expanded configuration, the sheath moving to a location to maintain said prosthesis distal portion in the compressed configuration while the cylindrical sleeve maintains said prosthesis proximal portion in the compressed configuration.

20. The introducer of claim 14, wherein the middle portion of said prosthesis radially moves to the expanded configuration while the cylindrical sleeve maintains said prosthesis proximal portion in the compressed configuration and the sheath maintains said prosthesis distal portion in the compressed configuration.

21. The introducer of claim 14, wherein the first region comprises a tube.

22. An introducer for an expandable endovascular prosthesis having a tubular member defining a lumen about a longitudinal axis, including a distal portion, a proximal portion having a self-expanding stent at a proximal end of said prosthesis proximal portion, and a middle portion between the proximal and distal portions, the prosthesis being radially movable between a compressed configuration and an expanded configuration, the introducer comprising:

a distal prosthesis positioning mechanism including a distal retention section positioned radially inside of a sheath to retain the prosthesis distal portion until deployment, and a first control member to selectively disengage the distal retention section from the prosthesis distal portion; and a proximal prosthesis positioning mechanism including a cylindrical sleeve to maintain the proximal self-expanding stent of said prosthesis in the compressed configuration until deployment, the cylindrical sleeve having a tapered extension extending proximally therefrom, and a second control member and a third control member to selectively disengage the proximal self-expanding stent from the cylindrical sleeve, wherein the second control member includes a first region coupled to the distal prosthesis positioning mechanism extending longitudinally therefrom, and a second region including an enlarged conical tip, the second region coupled to the first region and extending longitudinally therefrom, the enlarged uninflatable conical tip positioned within said prosthesis lumen and having a conical surface facing the proximal direction, said conical surface selectively abutting a distal end of the proximal self-expanding stent of said prosthesis to retain the proximal self-expanding stent in the cylindrical sleeve, and wherein the third control member is attached to the tapered extension of the cylindrical sleeve, the third control member being slidably engaged with the second control member to selectively disengage the cylindrical sleeve from said prosthesis by proximal movement of the cylindrical sleeve until the prosthesis proximal portion radially moves to the expanded configuration; and the sheath positioned radially outside of the cylindrical sleeve and contacting the distal and middle portions of said prosthesis to retain the distal and middle portions of said prosthesis in the compressed configuration until deployment.

23. The introducer of claim 22 further comprising a first control arrangement and a second control arrangement each to control a length, an axial position and an angular position of said prosthesis at a desired site in a body vessel lumen, the first control arrangement including a selective engagement of the first control member of the distal retention section with said prosthesis distal portion while retaining the second control member of said prosthesis proximal portion in the cylindrical sleeve, and the second control arrangement including selective movement of the third control member.

24. The introducer of claim 22, wherein said prosthesis is releasable from the cylindrical sleeve to radially expand from the compressed configuration to the expanded configuration without a trigger wire by withdrawal of the second control member and the enlarged conical tip distally from the abutting relationship and proximal movement of the third control member.

25. The introducer of claim 22, wherein the middle portion of said prosthesis radially moves to the expanded configuration while the cylindrical sleeve maintains said prosthesis proximal portion in the compressed configuration and the sheath maintains said prosthesis distal portion in the compressed configuration.

26. The introducer of claim 22, wherein the distal retention section, the first region and the second region including the enlarged conical tip are formed from a first tube, and wherein the third control member is formed from a second tube positioned radially inward from the first tube, the first and second tubes being concentric about the longitudinal axis.

27. The introducer of claim 26, wherein the second control member further includes a first control section coupled to the first tube, and the third control member further includes a second control section coupled to the second tube, both of the first and second control sections are maintained external to a patient.

28. The introducer of claim 27, wherein the first control member comprises a distal trigger wire coupled to a distal wire release mechanism maintained external to the patient, the distal trigger wire extending through the first tube, through an aperture of the distal retention section, and into a loop of said prosthesis, wherein the distal retention section is selectively disengaged from the distal portion of said prosthesis by removal of the distal trigger wire from the loop.

* * * * *